United States Patent
Murphy et al.

(10) Patent No.: US 6,759,032 B2
(45) Date of Patent: Jul. 6, 2004

(54) ANTIPERSPIRANT COMPOSITIONS CONTAINING FILM-FORMING POLYMERS

(75) Inventors: C. Shawn Murphy, Cincinnati, OH (US); Kristin Ann Boyle, Corona del Mar, CA (US); Eric S. Abrutyn, Anderson, OH (US)

(73) Assignee: The Andrew Jergens Company, Cincinnati, OH (US)

( * ) Notice: Subject to any disclaimer, the term of this patent is extended or adjusted under 35 U.S.C. 154(b) by 0 days.

(21) Appl. No.: 10/120,624

(22) Filed: Apr. 11, 2002

(65) Prior Publication Data

US 2003/0194387 A1 Oct. 16, 2003

(51) Int. Cl.[7] .............................. A61K 7/32; A61K 7/34; A61K 7/38; A61K 7/00
(52) U.S. Cl. .............................. 424/65; 424/66; 424/68; 424/400; 424/401
(58) Field of Search .............................. 424/65, 66, 68, 424/400, 401

(56) References Cited

U.S. PATENT DOCUMENTS

| | | |
|---|---|---|
| 4,743,441 A | 5/1988 | Takema et al. |
| 4,803,195 A | 2/1989 | Holzner |
| 5,508,024 A | 4/1996 | Tranner |
| 5,614,179 A | 3/1997 | Murphy et al. |
| 5,626,856 A | 5/1997 | Berndt |
| 5,880,250 A | 3/1999 | Housel et al. |
| 5,945,085 A | 8/1999 | Salas et al. |
| 5,965,116 A | 10/1999 | Mondet et al. |
| 5,989,570 A | 11/1999 | Lion et al. |
| 6,103,822 A | 8/2000 | Housel et al. |
| 6,106,813 A | 8/2000 | Mondet et al. |
| 6,113,882 A | 9/2000 | Mougin et al. |
| 6,428,777 B1 * | 8/2002 | Boyle et al. .................. 424/65 |

FOREIGN PATENT DOCUMENTS

WO    WO 99/51192    10/1999

OTHER PUBLICATIONS

Inolex website product description of Lexorez® TC–8, TC–15 and TL–8.

* cited by examiner

*Primary Examiner*—Shelley A. Dodson
(74) *Attorney, Agent, or Firm*—Frost Brown Todd LLC

(57) ABSTRACT

Antiperspirant compositions for topical application are disclosed. These compositions show improved antiperspirant efficacy, while providing minimized skin residue as well as good skin feel when applied. These antiperspirant compositions comprise an effective amount of an antiperspirant active, from about 10% to about 60% of a topical carrier, and from about 0.5% to about 10% of a non-toxic, water-insoluble, occlusive film-forming polyester polymer.

19 Claims, No Drawings

ANTIPERSPIRANT COMPOSITIONS CONTAINING FILM-FORMING POLYMERS

TECHNICAL FIELD

The present invention relates to topical compositions which, when applied to the human body, provide an antiperspirant benefit to the user.

BACKGROUND OF THE INVENTION

Antiperspirant products are widely used personal care products throughout the world. The primary benefit of these products, of course, is their ability to suppress perspiration and related odors on the body of the user. Antiperspirant products are applied to the skin and generally comprise an antiperspirant active which acts to inhibit excretion of perspiration from the eccrine glands.

It has long been desired to improve the efficacy of topical antiperspirant compositions in order that users experience less perspiration wetness. Further, if the efficacy of such products can be improved, it may be possible to formulate products in which the concentration of the antiperspirant active component can be reduced while still providing products of equal or even higher efficacy. This could lead to such products being less expensive, easier to formulate (by virtue of a reduced amount of antiperspirant active used), or generally having improved sensory and consumer-perceived dryness properties. The present invention accomplishes this result, and also may permit the formulation of compositions which are aesthetically pleasing and leave minimized white residue when applied to the skin. This is accomplished by utilizing film-forming polyester materials together with conventional antiperspirant actives.

The use of film-forming polymers generally in cosmetic and beauty care products is known in the art.

U.S. Pat. No. 4,743,441, Takema et al., issued May 10, 1988, discloses the use of a film-forming material in a cosmetic composition such as a facial pack, nail enamel or eyeliner. The film-forming material comprises a copolymer of vinyl alcohol and alkyl vinyl ether. Antiperspirant compositions are not disclosed.

U.S. Pat. No. 5,508,024, Tranner, issued Apr. 16, 1996, describes an antiperspirant composition which includes an alkyl olefinic acid amide/olefinic acid or ester copolymer. The composition is applied topically, forming a film on the user. The film is taught to effectively block the flow of perspiration. The Tranner patent teaches that the film can be used together with antiperspirant active materials. There is no suggestion that the film acts to enhance efficacy of the antiperspirant active itself. Further, polyester copolymers are not taught or suggested as the polymer material used.

U.S. Pat. No. 6,106,813, Mondet et al., issued Aug. 22, 2000, describes a class of film-forming polyester-polyurethane polymers. It is taught that these materials can be used in cosmetic products such as eyeliner, hair styling lotion, mascara or nail varnish. The Mondet patent discloses a laundry list of what are described as conventional cosmetic additive materials; antiperspirant actives are included on that list. No antiperspirant compositions are specifically discussed or exemplified. See also U.S. Pat. No. 5,989,570, Lion et al., issued Nov. 23, 1999; U.S. Pat. No. 6,113,882, Mougin et al., issued Sep. 5, 2000; and U.S. Pat. No. 5,965,116, Mondet et al., issued Oct. 12, 1999.

U.S. Pat. No. 5,614,179, Murphy et al., issued Mar. 25, 1997, describes the inclusion of sodium bicarbonate particles in a deodorant/antiperspirant stick composition. The sodium bicarbonate particles are coated with a combination of film-forming polymer and fragrance. The composition does not form a film on the skin of the user. See also U.S. Pat. No. 5,955,085, Salas et al., issued Aug. 31, 1999.

U.S. Pat. No. 5,626,856, Berndt, issued May 6, 1997, discloses personal care compositions which contain a volatile silicone, starch and glyceride ester. When the composition is applied topically, the volatile silicone is taught to evaporate leaving a translucent film on the skin. Antiperspirant compositions are specifically disclosed and exemplified. The film is said to work as a delivery vehicle for cosmetic and pharmaceutical actives. The film utilized in the Berndt patent is not a polyester material.

U.S. Pat. No. 4,803,195, Holzner, issued Feb. 7, 1989, describes antiperspirant compositions which include an encapsulated perfume base together with an antiperspirant active. Moisture from the body of the user is taught to release a portion of the perfume from the capsules. The capsules then re-form around the remainder of the perfume, preventing a negative interaction between the antiperspirant active and the perfume component. The capsules are not formed from a polyester material.

U.S. Pat. No. 5,880,250, Housel et al., issued Aug. 15, 2000, describes polymeric acid-functional polyols which include pendant hydroxyl and carboxyl groups. The materials are taught to be useful in forming polyurethanes. There is no suggestion to use these materials in topical personal care products or in combination with antiperspirant actives. See also U.S. Pat. No. 6,103,822, Housel et al., issued Aug. 15, 2000. Further, Inolex sells products under the tradename Lexorez including such polyesters as TC-8, TC-15 and TL-8. The Inolex website discloses that TC-8 is a copolymer of trimethylpentanediol, adipic acid and isononanoic acid. It is also disclosed that TC-8 may be included in topical personal care products and that, in those products, the film formed by this material acts to increase the partitioning of alpha- or beta-hydroxy acids or self-tanning agents from the products into the stratum corneum. There is no suggestion to include these materials in antiperspirant compositions.

International Published PCT Application WO 99/51192, Colgate-Palmolive Company, published Oct. 14, 1999, describes cosmetic compositions, including antiperspirant compositions, which comprise an active ingredient, a silicone gel material containing an elastomer, and at least one high HLB surfactant. It is taught that this composition provides reduced film formation when applied to the skin. The patent further teaches that reduced film formation increases availability of the active ingredient to penetrate into the skin, and is therefore desirable. Thus, this application teaches away from the inclusion of film-formers in antiperspirant compositions.

It has now been found that the inclusion of polyester film-forming materials and antiperspirant actives in antiperspirant compositions provides enhanced efficacy from those actives. This allows the compositions to be formulated with lower levels of antiperspirant active to achieve equivalent performance or with conventional levels of antiperspirant active to achieve enhanced performance. The inclusion of these polyester materials can also reduce the formation of white residue on the skin after all carrier materials have evaporated. Finally, these compositions have good skin feel characteristics.

SUMMARY OF THE INVENTION

The present invention relates to topical antiperspirant compositions comprising:

(a) a safe and effective amount (such as from about 1% to about 35%) of an antiperspirant active;
(b) from about 10% to about 60% of a topical carrier (such as a volatile silicone material); and (c) from about 0.5% to about 10% of a non-toxic, water-insoluble, occlusive, film-forming polyester polymer.

The method of minimizing perspiration on the human body through the application of the above-described composition is also included within the present invention. Finally, the present invention encompasses a method of minimizing perspiration in humans by applying topically an effective amount of antiperspirant active together with a polyester film which acts as an occlusive agent for the antiperspirant active.

All percents and ratios given herein are "by weight" unless otherwise specified.

All patents and publications noted in this application are incorporated herein by reference.

DETAILED DESCRIPTION OF THE INVENTION

The topical antiperspirant compositions of the present invention include an antiperspirant active material, a topical carrier, and a film-forming polyester material, and may optionally contain additional components conventionally found in topical antiperspirant compositions. Each of those components, as well as the method of making and using the compositions of the present invention, will be discussed in detail below.

The compositions of the present invention may be formulated in the variety of product forms conventionally used for antiperspirant compositions including, for example, solids, liquids (e.g., roll-ons), soft solids, creams and gels. The topical carrier and adjunct optional ingredients used in these compositions will likely differ based on the particular product form selected. The particular components to be included, as well as the levels of those components and formulation techniques, to achieve particular product forms are well known to those skilled in the antiperspirant arts. The preferred compositions of the present invention are solids, such as solid sticks, extrudable soft solids and clear extrudable gels.

The present invention contains a safe and effective amount of an antiperspirant active material. Generally, the compositions will include from about 1% to about 35%, preferably from about 5% to about 26% of the antiperspirant active material. The invention described herein may permit the formulation of antiperspirant products which include lower levels of antiperspirant active than those conventionally used in such products. In the alternative, the compositions of the present invention can enhance antiperspirant performance above that typically seen with the standard active levels conventionally found in antiperspirant products. The weight percentages stated herein are calculated on an anhydrous metal salt basis (exclusive of glycine, the salts of glycine, or other complexing agents). The antiperspirant materials preferably have a particle size ranging from about 1 to about 100 microns, more preferably from about 1 to about 50 microns for anhydrous systems. They may be impalpable (micronized) or microspherical in form.

Any antiperspirant materials known in the art which act on secretion of the eccrine glands may be used in the present invention. Such materials include, for example, many aluminum or zirconium astringent salts or complexes. Examples of useful antiperspirant materials are described in U.S. Pat. No. 6,287,544, Franklin et al., issued Sep. 11, 2001; U.S. Pat. No. 6,261,543, Fletcher et al., issued Jul. 17, 2001; and U.S. Pat. No. 6,187,301, Scavone et al., issued Feb. 13, 2001; all incorporated herein by reference.

As used herein, "safe and effective amount" of antiperspirant active is intended to include levels of active which are sufficiently high to provide an antiperspirant benefit to the user when applied topically, but not so high as to cause undesirable side effects, such as skin irritation.

Aluminum salts of the type useful herein include aluminum chloride and the aluminum hydroxyhalides having the general formula $Al_2(OH)_xQ_y \cdot XH_2O$ where Q is chlorine, bromine or iodine; where x is from about 2 to about 5, and x+y=about 6 wherein x and y do not need to be integers; and where X is from about 1 to about 6. Aluminum salts of this type can be prepared in the manner described more fully in U.S. Pat. No. 3,887,692, Gilman, issued Jun. 3, 1975, and U.S. Pat. No. 3,904,741, Jones and Rubino, issued Sep. 9, 1975, both incorporated herein by reference.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

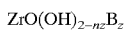

wherein z may vary from about 0.9 to about 2 and need not be an integer, n is the valence of B, 2−nz is greater than or equal to 0, and B may be selected from the group consisting of halides, nitrate, sulfamate, sulfate, and mixtures thereof. Although only zirconium compounds are exemplified in this context, it will be understood that other Group IV B metal compounds, including hafnium, could be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than 0 groups per molecule.

Several types of antiperspirant complexes utilizing the above antiperspirant salts are known in the art. For example, U.S. Pat. No. 3,792,068, Luedders et al., issued Feb. 12, 1974, incorporated herein by reference, discloses complexes of aluminum, zirconium and amino acids such as glycines. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a metal:Cl ratio of from about 0.73 to about 1.93.

Preferred ZAG complexes are formed by:
(A) co-dissolving in water
  (1) one part $Al_2(OH)_{6-m}Q_m$, wherein Q is an anion selected from the group consisting of chloride, bromide and iodide, and m is a number from about 0.8 to about 2.0;
  (2) x parts $ZrO(OH)_{2-a}Q_a \cdot nH_2O$, where Q is chloride, bromide or iodide; where a is from about 1 to about 2; where n is from about 1 to about 8; and where x has a value of from about 0.16 to about 1.2; and
  (3) p parts neutral amino acid selected from the group consisting of glycine, dl-tryptophane, dl-β-phenylalanine, dl-valine, dl-methionine and β-alanine, and where p has a value of from about 0.06 to about 0.53;
(B) co-drying the resultant mixture to a friable solid; and
(C) reducing the resultant dried inorganic-organic antiperspirant complex to particulate form.

A preferred aluminum compound for preparation of such ZAG type complexes is aluminum chlorhydroxide of the empirical formula $Al_2(OH)_5Cl.2H_2O$. Preferred zirconium compounds for preparation of such ZAG-type complexes are zirconyl hydroxychloride having the empirical formula $ZrO(OH)Cl.3H_2O$ and the zirconyl hydroxyhalides of the empirical formula $ZrO(OH)_{2-a}Cl_2.nH_2O$ wherein a is from about 1.5 to about 1.87, and n is from about 1 to about 7. The preferred amino acid for preparing such ZAG-type complexes is glycine of the formula $CH_2(HN_2)COOH$. Salts of such amino acids can also be employed in the antiperspirant complexes. See U.S. Pat. No. 4,017,599, Rubino, issued Apr. 12, 1977, incorporated herein by reference.

A wide variety of other types of antiperspirant complexes are also known in the art. For example, U.S. Pat. No. 3,903,258, Siegal, issued Sep. 2, 1975, discloses a zirconium aluminum complex prepared by reacting zirconyl chloride with aluminum hydroxide and aluminum chlorhydroxide. U.S. Pat. No. 3,979,510, Rubino, issued Sep. 7, 1976, discloses an antiperspirant complex formed from certain aluminum compounds, certain zirconium compounds, and certain complex aluminum buffers. U.S. Pat. No. 3,981,896, issued Sep. 21, 1976, discloses an antiperspirant complex prepared from an aluminum polyol compound, a zirconium compound and an organic buffer. U.S. Pat. No. 3,970,748, Mecca, issued Jul. 20, 1976, discloses an aluminum chlorhydroxy glycinate complex of the approximate general formula $[Al_2(OH)_4Cl][H_2CNH_2—COOH]$. All of these patents are incorporated herein by reference.

Of all the above types of antiperspirant actives, preferred compounds include the 5/6 basic aluminum salts of the empirical formula $Al_2(OH)_5Cl.2H_2O$; mixtures of $AlCl_3.6H_2O$ and $Al_2(OH)_5Cl.2H_2O$ with aluminum chloride to aluminum hydroxychloride weight ratios of up to about 0.5; ZAG-type complexes wherein the zirconium salt is $ZrO(OH)Cl.3H_2O$, the aluminum salt is $Al_2(OH)_5Cl.2H_2O$ or the aforementioned mixtures of $AlCl_3.6H_2O$ and $Al_2(OH)_5 Cl.2H_2O$ wherein the total metal to chloride molar ratio in the complex is less than about 1.25, the Al:Zr molar ratio is about 3.3, and the amino acid is glycine; and ZAG-type complexes wherein the zirconium salt is $ZrO(OH)_{2-a} Cl_a.nH_2O$ wherein a is from about 1.5 to about 1.87 and n is from about 1 to about 7, the aluminum salt is $Al_2(OH)_5 Cl.2H_2O$, and the amino acid is glycine.

Preferred particulate antiperspirant materials include inorganic or organic salts of aluminum, zirconium or zinc, as well as mixtures of those materials. Aluminum chlorhydrate (ACH) actives and aluminum zirconium tetrachlorohydrex glycine complex are particularly preferred antiperspirant actives for use in the present invention, with the aluminum zirconium tetrachlorohydrex glycine complex being particularly preferred.

Topical carriers for use in antiperspirant compositions are well known to those skilled in the art. The nature and amount of the carriers used will vary depending on the specific form of the composition to be formulated. The carriers utilized must be satisfactory for topical application under occlusion and must be compatible with the other components contained in the antiperspirant formulation. The carriers used will generally be volatile hydrocarbons or volatile silicone materials.

Volatile hydrocarbon solvents (such as dodecene) and silicone solvents are well-known for use in antiperspirant cosmetic and deodorant compositions. Volatile silicones known for use in antiperspirant compositions are preferred for use in the present invention. The volatile silicone material is preferably either a cyclic or a linear polydimethylsiloxane and is present at a level of from about 10% to about 60%, preferably from about 20% to about 50%, of the composition.

The cyclic polydimethylsiloxanes preferably include from about 3 to about 7 silicon atoms, more preferably from about 4 to about 6 silicon atoms. The general formula for such siloxanes is

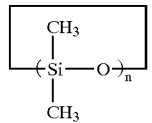

wherein n is from about 3 to about 7. The linear volatile polydimethylsiloxanes contain from about 2 to about 9 silicon atoms and have the general formula $(CH_3)_3Si$—$O$$[Si(CH_3)_2$—$O]n$-$Si(CH_3)_3$, wherein n is from about 0 to about 7.

Silicones of the above type are commercially available, for example, from Dow Corning Corporation (Dow Corning 344, 345, 200 and 1184 fluids), Union Carbide (Silicone 7207 and Silicone 7158), and Stauffer Chemical (SWS-03314), as well as from General Electric Specialty Chemicals.

The linear volatile silicone materials generally have viscosities of less than about 5 centistokes at 25° C., while the cyclic materials have viscosities less than about 10 centistokes. "Volatile" means that the material has a measurable vapor pressure. A description of volatile silicones is found in Todd and Byers, "Volatile Silicone Fluids for Cosmetics", Cosmetics and Toiletries, 91:27–32 (1976), incorporated herein by reference.

Cyclic polydimethylsiloxanes, and particularly cyclomethicone D-5 (decamethylcyclopentasiloxane) and D-6 (tetradecamethylcyclohexasiloxane), are preferred for use in the compositions of the present invention.

The compositions of the present invention also include a non-toxic, water-insoluble, occlusive, film-forming polyester polymer material. The polyester polymer is one which forms a film on the skin upon evaporation of the volatile solvent; the film provides an occlusive barrier on the skin. The polyester material must be non-toxic and non-irritating to the skin and it must be compatible with the other components included in the antiperspirant composition. The polyester polymer is included in the compositions at levels from about 0.5% to about 10%, preferably from about 0.5% to about 7.5%, more preferably from about 1% to about 5%, by weight of the composition.

A preferred group of polyester materials includes a backbone derived from the reaction of a linear or branched-chain multifunctional hydroxy-containing reactant (i.e., diols, polyols, carbohydrates, preferably a diol) with a linear or branched chain multifunctional carboxylic acid or anhydride (preferably a diacid). They can be further end-capped with a monofunctional acid or hydroxy-containing component. Such polymers typically have a molecular weight of from about 500 to about 100,000.

Preferred carboxylic acids or anhydrides for use in forming these polymers include adipic acid, succinic acid or anhydride, sebasic acid or anhydride, phthalic acid or anhydride, isophthalic acid, tetraphthalic acid, pyromellitic anhydride or dianhydride, trimellitic anhydride, and mixtures of these materials.

Preferred multifunctional hydroxy-containing compounds for use in forming these polymers include propylene glycol, dipropylene glycol, butanediol, tripropylene glycol, hexanediol, polyoxyethylene glycol, neopentyl glycol, trimethylpentanediol, pentaerythritol, dipentanerythritol, glycerin, methyl glucoside, sucrose, and mixtures of these materials.

Particularly preferred materials are those commercially available under the tradename Lexorez TC-8 and TC-15, commercially available from Inolex. These materials are described in U.S. Pat. No. 5,880,250, Housel et al., issued Mar. 9, 1999, and U.S. Pat. No. 6,103,822, Housel et al., issued Aug. 22, 2000, both incorporated herein by reference. Lexorez TC-8 and TC-15 are trimethylpentanediol/adipic acid/isononanoic acid copolymers. Lexorez TC-8 is a trimethylpentanediol/adipic acid copolymer. Without intending to be bound by theory, it is believed that the film formed by the polyester polymer on the surface of the skin upon evaporation of the volatile solvent. This film acts as an occlusive barrier for the antiperspirant active on the skin, which enhances the efficacy of that active.

The compositions of the present invention may also contain optional components, conventionally used in antiperspirant compositions, which modify the physical characteristics of the antiperspirant composition or components of that composition or serve as "active" components when deposited on the skin in addition to the antiperspirant active material. Examples of such additional actives include deodorant materials, bacteriostats and fungistats. Optional components useful herein are described in the following documents, all incorporated by herein by reference: U.S. Pat. No. 4,049,792, Elsnau, issued Sep. 20, 1977; Canadian Patent 1,164,347, Beckmeyer et al., issued Mar. 27, 1984; European Patent Specification 117,070, May, published Aug. 29, 1984; Geria, "Formulation of Stick Antiperspirants and Deodorants", Cosmetics and Toiletries, 99:55–60 (1984); and Rieger, M. (ed.), *Harry's Cosmetology*, $8^{th}$ edition, Chemical Publishing Company, 2000, chapter 21.

The specific nonactive components that may be used in the present invention will depend upon the characteristics desired for the particular compositions. These components are used at their art-established levels to achieve their art-established benefits. Such components include, for example, structurants, thickeners and other viscosity modifiers, emollients, colorants, perfumes, emulsifiers, surfactants, preservatives, fillers, and skin feel enhancers.

Among the optional components that may be included in the compositions of the present invention are structurant materials which provide viscosity to cream, gel and soft solid products, and structure to solid products. When used, the structurant material is present in the compositions of the present invention at from about 12% to about 30%, preferably from about 10% to about 25%, of the total composition. The structurant materials are materials which are appropriate for topical administration, compatible with other ingredients in the formulation, and have a melting point of at least about 40° C. They are generally selected from high melting point and low melting point waxes, and mixtures of those materials (although other well-known structurant materials may be used). Examples of structurant materials useful in the present invention include $C_{14}$–$C_{40}$ fatty alcohols, polyethylenes, alkyl ($C_{18}$–$C_{45}$) methylsiloxanes, jojoba ester waxes, hydrogenated vegetable oils, and mixtures thereof. High melting point waxes (65–101° C.) include such materials as beeswax, montan, ozokerite, ceresin, paraffin, hydrogenated castor oil, and $C_{26}$–$C_{50}$ linear alcohols. Low melting point waxes (40–65° C.) include such materials as $C_{14}$–$C_{25}$ fatty alcohols, fatty esters and fatty amides, particularly stearyl alcohol, cetyl alcohol, stearic acid, and polydimethylsiloxanyl beeswax. $C_{16}$–$C_{22}$ fatty alcohols are preferred low melting point waxes. Preferred structurant materials include stearyl alcohol, hydrogenated castor oil, and mixtures of stearyl alcohol and hydrogenated castor oil.

The compositions of the present invention may also include thickeners, such as polyethylene materials, silicas (both fumed and unfumed), talc, starches, clay materials, and mixtures of these thickeners. Thickeners are generally present in the compositions of the present invention at from about 0.5% to about 10% of the composition, preferably from about 0.5% to about 7% of the total composition.

One thickener which may be used in the present invention is a clay component, as well as an activator for the clay. When used, the clays are generally present at from about 0.5% to about 7%, preferably from about 1% to about 5%, of the total composition.

Clay materials suitable for use in the compositions of the present invention are selected from montmorillonite clays and hydrophobically-treated montmorillonite clays. Montmorillonite clays are those which contain the mineral montmorillonite and are characterized by having a suspending lattice. Examples of these clays include the bentonites, hectorites, and colloidal magnesium aluminum silicates, as well as mixtures of those materials.

Bentonite is colloidal, hydrated aluminum silicate obtained from montmorillonite and has the formula $Al_2O_3.4SiO_2.H_2O$. A more detailed discussion of bentonites can be found in the Kirk-Othmer Encyclopedia of Chemical Technology, $2^{nd}$ Ed., Vol. 3 (1964), pp. 339–360, published by Interscience Publishers, which is incorporated herein by reference.

Hectorite, also a montmorillonite clay, differs from bentonite in that there is almost a complete substitution of aluminum in the lattice structure of bentonite by magnesium. In addition, hectorites contain lithium and fluorine. Barasym NAH-100 is an example of a commercially available synthetic hectorite marketed by NL Industries, Inc.

The magnesium aluminum silicates are complexes of colloidal magnesium aluminum silicate richer in magnesium than aluminum. Magnesium aluminum silicates are commercially available as Veegum (R.T. Vanderbilt Co.).

Examples of clay materials which are preferred for use in the present invention include certain hydrophobically-treated montmorillonite clays, e.g., hydrophobic bentonites available under the tradename of "Bentone" and "Tixogel." These organo-modified clays are prepared by reacting bentonite or hectorite in a cation exchange system with an amine. Different amines are reacted to obtain a variety of organo-modified clays, which may also differ in proportions of $SiO_2$, MgO and $Al_2O_3$. Specific examples of Bentones are Bentone 38, Bentone 34, Bentone 27, Bentone 14, and Bentone LT, all of which have a particle size of below about 5 microns and are commercially available from Elementis Specialties (formerly Rheox, NL Industries and National Lead Company). Bentone 38 is a preferred suspending/thickening agent and is described in greater detail in the Technical Bulletin from the National Lead Company entitled "BENTONE 38" (incorporated by reference).

Another preferred clay material for use in the present invention is quaternium-18 hectorite.

The clay are used together with activators to help them swell and thicken the antiperspirant compositions. Activators for the clay are typically used at levels of from about 0.2% to about 1.5%, preferably from about 0.25% to about 1.25%, of the total composition. The activators are generally polar compounds which chemically activate the clay materials. Examples of such polar activators include propylene carbonate, ethanol, and mixtures of those materials. The clays and activators may be incorporated separately or may be purchased as a mixture of clay, activator and a solvent. For example, Bentone Gel VSSV, commercially available from Elementis Specialties, is a mixture of about 77% cyclomethicone, 18% quaternium-18 hectorite and 5% SDA-40 alcohol (ethanol).

The compositions of the present invention may also include emollients, well-known in the art, such as fatty acid esters (for example, $C_{12-15}$ alkyl benzoate, diisopropyl adipate, or neopentyl glycol diheptanoate), long chain ethers (for example PPG-14 butyl ether), and silicone materials (for example dimethicone, phenyl trimethicone, cetyl dimethicone). When used, such materials are included at from about 2% to about 20% of the total composition.

Finally, the compositions of the present invention may contain from about 0.5% to about 10%, preferably from about 1% at about 5%, of a botanical extract which is compatible with the skin and with the remainder of the antiperspirant formulation, and which provides a cosmetic or aesthetic benefit to the skin. Examples of plant extracts which can be used in the present invention include ginger rhizome, almond, birch, clove, rose hip, white birch, gambi, burnet, hiba, willow herb, *Phellodendron Amurense, Coptis Chinesis*, clove oil extract, tea tree oil, olive leaf extract, rosemary extract, fennel seed, phytoplenolin, sericin, K2 glycerrizinate, capsaicin, menthol and menthyl lactate. Preferred materials include ginger extract, burnet extract, and mixtures of those materials. A particularly preferred material is ginger root extract (*Zingiber Officinale*), which can reduce the diameter and length of underarm hair and therefore decrease the amount of shaving required by the user.

The antiperspirant stick of the present invention may be manufactured using methods known in the art, for example, as described in the following examples.

The antiperspirant compositions of the present invention are used in a conventional manner. Specifically, the compositions may be used to prevent and/or control perspiration wetness or body odor by topically applying, one or more times a day, an effective amount of the composition to areas of the body particularly prone to perspiration or odor (for example, the underarm or axillary area). Typically, from about 0.50 to about 50 mg/cm$^2$ of composition is applied to the axilla skin. In addition, the present invention encompasses a method of minimizing perspiration in humans by applying an effective amount of antiperspirant active (for example, from about 0.10 to about 12.5 mg/cm$^2$ of active) to areas of the body prone to perspiration, together with a polyester film, as described herein, which acts as an occlusive agent for the antiperspirant active material.

The following nonlimiting examples illustrate the compositions, methods of making, and methods of using the present invention described in this application.

EXAMPLES

Antiperspirant stick compositions of the present invention, having the compositions given in the following table, are formulated using the procedure described herein. The compositions are stable, provide good antiperspirant performance with good skin feel and minimized skin whitening.

A clear gel formulation of the present invention is made as follows: Each phase is made up and adjusted to match refractive index within ±0.0005. The aqueous-containing phase is added slowly into the cyclomethicone-containing phase using mild turbulent mixing at room temperature. The addition should occur over at least 15 minutes. Any other materials (e.g., fragrance) can be added to this emulsion and mixed for 5 minutes to assure uniform dispersion. Optionally, moderate one-pass shear can be used to reduce particle size of dispersed aqueous phase and increase viscosity to the desired end result.

|  | Example 1 |
|---|---|
| Cyclomethicone-Containing Phase | |
| Cyclopentasiloxane | 11.0 |
| Trimethylpentanediol/adipic acid/isononanoic acid copolymer | 2.0 |
| Hydrogenated Polydecane | 3.0 |
| Dimethicone Copolyol (as Abil EM-97) | 1.0 |
| Methyl Glucoside-20 Benzoate | 1.00 |
| Aqueous Phase | |
| Dipropylene Glycol | 16.25 |
| Deionized Water | 11.25 |
| Aluminum Zirconium Chlorohydrex-Glycinate (Summit AzG 442) | 54.50 |

By modifying the ratio of cyclomethicone-containing phase to aqueous-containing phase, one can produce roll-ons or pump sprays.

Liquid antiperspirant compositions of the present invention having the components given below are formulated as follows:

The liquid antiperspirant compositions described herein can be produced by conventional processes for antiperspirant roll-on compositions. A convenient process sequence for liquid antiperspirant formulations comprises first mixing a thickener material and activator with the topical volatile carrier. Typically, some type of homomixing is needed to form a homogenous mixture. The firm-forming polyester polymer material is then blended into the topical carrier. Thereafter, particulate antiperspirant active can be blended with the carrier solution and mixed until homogenous. Emollients, essential and optional components are blended into the carrier solution. Processing temperatures will generally range from about 50° C. to about 125° C. After the mixture is homogenous, it is introduced into a dispensing container.

| | Example | | | | |
|---|---|---|---|---|---|
| Ingredient Name | 2 % | 3 % | 4 % | 5 % | 6 % |
| Cyclomethicone | 45.00 | 46.75 | 49.50 | 51.00 | 49.00 |
| Quaternium-18 Hectorite | 5.00 | 5.00 | 3.00 | 3.00 | 3.00 |
| Propylene Carbonate | 1.00 | 1.00 | NA | NA | NA |
| Ethanol | NA | NA | 1.00 | 1.00 | 0.75 |
| Dipropylene Glycol | NA | NA | 1.00 | 1.00 | 1.00 |
| PPG-3 Myristyl Ether | 2.00 | 2.00 | NA | NA | NA |
| Polyethylene | 3.00 | 3.00 | 2.00 | 2.00 | 1.00 |
| Petrolatum | 4.75 | 2.25 | 4.50 | 5.00 | 9.25 |
| Mineral Oil | 10.00 | 10.00 | 8.00 | 8.00 | 6.00 |
| Dimethicone Copolyol | 0.75 | 1.00 | NA | NA | NA |
| Silicone Elastomer | 1.00 | 0.50 | 2.00 | 2.00 | 1.00 |
| Cetearyl Ethylhexanoate | 1.00 | 1.00 | 2.00 | 1.50 | 1.50 |
| Aluminum Zirconium Tetrachlorohydrex Glycinate | 24.00 | 24.00 | 24.00 | 24.00 | 24.00 |
| Trimethylpentanediol/ Adipic Acid/Isononanoic Acid Copolymer | 2.00 | 3.00 | 2.50 | 1.00 | 3.00 |
| Fragrance | 0.50 | 0.50 | 0.50 | 0.50 | 0.50 |
| TOTAL | 100.00 | 100.00 | 100.00 | 100.00 | 100.00 |

Soft-solid (cream) antiperspirant compositions of the present invention having the components given below are formulated as follows:

Soft-solid (cream) compositions of this invention can be produced by processes which involve forming a heated mixture of the composition at a temperature such that the structurant is in solution in the topical volatile carrier phase, pouring that mixture into a mold, which may take the form of a dispensing container, and then cooling the mixture whereupon the structurant solidifies within the carrier phase, and thereby gels that phase and hence the whole composition.

A preferred method for processing the antiperspirant cream compositions described herein utilizes conventional processes for antiperspirant cream compositions followed by a solidification step. A conventional process sequence for cream antiperspirant formulations comprises first mixing a thickener material with the topical volatile carrier. Typically, some type of homomixing is needed to form a homogenous mixture. The structurant or mixture of structurants, namely the wax(es) and the film-forming polyester polymer are then blended into the topical carrier mixture at a temperature that is high enough to melt the structurant. Thereafter, particulate antiperspirant active can be blended with the carrier solution and mixed until homogenous. Emollients, essential and optional components are blended into the carrier solution. Processing temperatures will generally range from about 50° C. to about 125° C. After the mixture is homogenous, the resulting mixture is introduced into a dispensing container, such as a dispensing canister. This is usually carried out at a temperature 5° to 30° C. above the setting temperature of the composition. The container and contents are then cooled to ambient temperature. Cooling may be brought about by nothing more than allowing the container and contents to air cool. Cooling may be assisted by blowing ambient or even refrigerated air over the containers and their contents.

| Ingredient Name | Example 7 % | 8 % | 9 % | 10 % |
|---|---|---|---|---|
| Cyclomethicone | 45.25 | 51.25 | 50.75 | 49.00 |
| Dimethicone (100 cs) | NA | 2.00 | 2.00 | NA |
| Colloidal Silicon Dioxide | 2.25 | 4.00 | 4.50 | 2.25 |
| Stearyl Alcohol | 2.00 | NA | NA | 2.00 |
| Hydrogenated Castor Oil MP-80 | 3.00 | 3.25 | NA | NA |
| PPG-14 Butyl Ether | NA | NA | 2.00 | NA |
| Fluid AP | NA | NA | 3.00 | NA |
| Petrolatum | 10.00 | NA | NA | 4.00 |
| PPG-3-Isosteareth-9 | NA | NA | 4.75 | NA |
| PPG-5-Cetheth-20 | NA | NA | 2.50 | NA |
| PEG-20 Sorbitan Isostearate | 1.00 | NA | NA | 1.00 |
| PPG-9 Steareth-3 | NA | 3.75 | NA | NA |
| Glyceryl Stearate and PEG-100 Stearate | 2.50 | 1.25 | NA | 2.50 |

-continued

| Ingredient Name | Example 7 % | 8 % | 9 % | 10 % |
|---|---|---|---|---|
| Bentone 38 VCG | NA | NA | NA | 3.25 |
| Propylene Carbonate | NA | NA | NA | 0.75 |
| Talc | 7.00 | 7.00 | NA | 7.00 |
| Corn Starch | NA | NA | 4.50 | NA |
| Trimethylpentanediol/Adipic Acid/Isononanoic Acid Copolymer | 2.50 | 3.00 | 1.50 | 0.75 |
| Aluminum Zirconium Tetrachlorohydrex-Gly Powder | 24.00 | 24.00 | 24.00 | 24.00 |
| Fragrance | 0.50 | 0.50 | 0.50 | 0.50 |
| TOTAL | 100.00 | 100.00 | 100.00 | 100.00 |

Solid antiperspirant compositions of the present invention having the components given below are formulated as follows:

The antiperspirant suspension solid stick compositions described herein can be produced by conventional processes for suspension solid stick compositions followed by a solidification step. A conventional process sequence for suspension antiperspirant formulations comprises first mixing the structurant or mixture of structurants, namely the wax(es) and the film-forming polyester polymer, with the topical volatile carrier at a temperature that is high enough to melt the structurant. Thereafter, particulate antiperspirant active can be blended with the carrier solution and mixed until homogenous. Thickeners, emollients, essential and optional components are blended into the carrier solution. Processing temperatures will generally range from about 50° C. to about 125° C. The suspensions solid stick compositions are formed into a solid mass by cooling, for example by being introduced into its dispensing container at a temperature that is often 5° to 10° C. above its normal setting temperature. The process normally includes a suitable filling process, such as a pour fill process (sometimes gravity-fed injection) or injection at elevated pressure into a dispensing container such as a barrel where it is cooled or allowed to cool to ambient. Cooling may be brought about by nothing more than allowing the container and contents to air cool. Cooling may be assisted by blowing ambient or even refrigerated air over the containers and their contents.

| Ingredient Name | Example 11 % | 12 % | 13 % | 14 % | 15 % | 16 % | 17 % | 18 % |
|---|---|---|---|---|---|---|---|---|
| Stearyl Alcohol | 7.00 | NA | 15.00 | NA | NA | 18.00 | 18.00 | 17.00 |
| Cetyl Alcohol | NA | NA | NA | 15.45 | 8.25 | NA | NA | NA |
| Myristyl Alcohol | NA | 6.25 | NA | NA | 7.00 | NA | NA | NA |
| PPG-14 Butyl Ether | 2.00 | NA | 4.00 | 7.00 | 4.00 | NA | 6.00 | 4.50 |
| Hydrogenated Polydecene | NA | 5.00 | NA | 4.00 | 3.00 | 9.00 | NA | V |
| C12–15 Alkyl Benzoate | 6.00 | NA | 5.00 | NA | NA | V | NA | 9.00 |
| Castor Wax | 3.00 | NA | 2.20 | NA | NA | 5.00 | 5.00 | 2.50 |
| Alkyl Dimethicone | NA | 2.50 | NA | NA | 3.25 | NA | NA | NA |
| Cyclomethicone | 45.50 | 45.50 | 39.30 | 39.30 | 34.50 | 34.50 | 31.50 | 37.25 |
| Fumed Silica | NA | NA | NA | 0.75 | 0.50 | 0.50 | NA | NA |
| Bentone | 5.00 | 5.00 | NA | NA | NA | NA | NA | 1.40 |
| Propylene Carbonate | 1.50 | 0.75 | NA | NA | NA | NA | NA | NA |
| Dry Flo | 4.50 | NA | 7.00 | NA | NA | NA | NA | NA |
| Talc | NA | 7.00 | NA | 5.00 | 9.00 | 7.00 | NA | NA |
| Aluminum Chlorhydrate | 24.00 | 24.00 | NA | NA | NA | NA | NA | NA |
| Aluminum Zirconium Tetrachlorohydrex Glycinate | NA | NA | 24.00 | 24.00 | 24.00 | 24.00 | 24.00 | 24.00 |

-continued

| Ingredient Name | Example | | | | | | | |
|---|---|---|---|---|---|---|---|---|
| | 11 % | 12 % | 13 % | 14 % | 15 % | 16 % | 17 % | 18 % |
| Polyethylene | NA | 1.00 | NA | NA | 1.00 | 2.00 | 5.00 | 2.50 |
| Trimethylpentanediol/Adipic Acid/Isononanoic Acid Copolymer | 1.00 | 2.50 | 3.00 | 4.00 | 5.00 | 2.50 | 2.00 | 1.00 |
| Fragrance | 0.50 | 0.50 | 0.50 | 0.50 | 0.50 | 0.50 | 0.50 | 0.50 |
| TOTAL | 100.00 | 100.00 | 100.00 | 100.00 | 100.00 | 100.00 | 100.00 | 100.00 |

What is claimed is:

1. A topical antiperspirant composition comprising:
   (a) a safe and effective amount of an antiperspirant active;
   (b) from about 10% to about 60% of a topical carrier; and
   (c) from about 0.5% to about 10% of a non-toxic, water-insoluble, occlusive film-forming polyester polymer.

2. The antiperspirant composition according to claim 1 which contains from about 1% to about 35% of the antiperspirant active.

3. The antiperspirant composition according to claim 2 wherein the antiperspirant active is selected from organic or inorganic salts of aluminum, zirconium, zinc, and mixtures thereof.

4. The antiperspirant composition according to claim 3 wherein the topical carrier is selected from volatile hydrocarbons, volatile silicones, and mixture thereof.

5. The antiperspirant composition according to claim 4 wherein the volatile silicone is selected from cyclic siloxanes containing from about 3 to about 7 silicon atoms and linear siloxanes containing from about 2 to about 9 silicon atoms.

6. The antiperspirant composition according to claim 5 wherein volatile silicone is selected from cyclic siloxanes containing from about 3 to about 7 silicon atoms.

7. The antiperspirant composition according to claim 6 wherein the antiperspirant active is an aluminum zirconium chlorohydrex glycine complex.

8. The antiperspirant composition according to claim 7 wherein the volatile silicone is selected from decamethylcyclopentasiloxane, tetradecamethylcyclohexasiloxane, and mixtures thereof.

9. The antiperspirant composition according to claim 1 in the form of a solid composition.

10. The antiperspirant composition according to claim 1 in the form of a liquid composition.

11. The antiperspirant composition according to claim 1 in the form of an extrudable solid or gel.

12. The antiperspirant composition according to claim 1 or claim 8 wherein the polymer has a backbone derived from the reaction of a linear or branched-chain multifunctional hydroxyl-containing compound with a linear or branched-chain multifunctional carboxylic acid or anhydride.

13. The antiperspirant composition according to claim 12 wherein the polymer has a molecular weight of from about 500 to about 100,000.

14. The antiperspirant composition according to claim 13 wherein, in the polymer component, the multifunctional carboxylic acid or anhydride reactant is selected from adipic acid, succinic acid or anhydride, sebasic acid or anhydride, phthalic acid or anhydride, isophthalic acid, tetraphthalic acid, pyromellitic anhydride or dianhydride, trimellitic anhydride, and mixtures thereof.

15. The antiperspirant composition according to claim 14 wherein, in the polymer component, the multifunctional hydroxyl-containing reactant is selected from trimethylpentanediol, neopentyl glycol, butanediol, glycerin, propylene glycol, dipropylene glycol, tripropylene glycol, hexylene glycol, trimethylpropanediol, hexanediol, polyoxyethylene glycol, pentaerythritol, dipentaerythritol, methyl glucoside, sucrose, and mixtures thereof.

16. The antiperspirant composition according to claim 15 wherein polymer is selected from trimethylpentanediol/adipic acid/isononanoic acid copolymers, trimethylpentandiol/adipic acid copolymers, and mixtures thereof.

17. The antiperspirant composition according to claim 15 which contains from about 0.5% to about 7.5% of the polymer component.

18. A method for minimizing perspiration in a human comprising applying an effective amount of the composition of claim 1 to the skin of said human.

19. A method for minimizing perspiration in humans comprising topically applying an effective amount of an antiperspirant active to the body of said human together with a polyester film which acts as an occlusive agent for the antiperspirant active on the skin.

* * * * *